(12) United States Patent
Orban et al.

(10) Patent No.: US 10,072,488 B2
(45) Date of Patent: Sep. 11, 2018

(54) APPARATUS, METHOD, AND SYSTEM FOR IDENTIFYING, LOCATING, AND ACCESSING ADDRESSES OF A PIPING SYSTEM

(71) Applicant: AOI (Advanced Oilfield Innovations, Inc.), Stafford, TX (US)

(72) Inventors: Andre Orban, Sugarland, TX (US); Daniel Maurice Lerner, Missouri City, TX (US); Barry Kent Holder, Montgomery, TX (US)

(73) Assignee: AOI (Advanced Oilfield Innovations), Stafford, TX (US)

( * ) Notice: Subject to any disclaimer, the term of this patent is extended or adjusted under 35 U.S.C. 154(b) by 0 days.

(21) Appl. No.: 15/458,147

(22) Filed: Mar. 14, 2017

(65) Prior Publication Data

US 2017/0298720 A1 Oct. 19, 2017

Related U.S. Application Data

(63) Continuation of application No. 14/668,128, filed on Mar. 25, 2015, now Pat. No. 9,631,470.

(51) Int. Cl.
*G01N 27/72* (2006.01)
*E21B 43/263* (2006.01)
(Continued)

(52) U.S. Cl.
CPC ............ *E21B 43/263* (2013.01); *E21B 47/00* (2013.01); *G01B 21/08* (2013.01); *G01N 21/00* (2013.01); *G01N 23/00* (2013.01); *G01N 27/02* (2013.01); *G01N 27/26* (2013.01); *G01N 27/72* (2013.01); *G01N 29/04* (2013.01)

(58) Field of Classification Search
USPC .......... 235/375; 345/633; 166/254.2; 175/40
See application file for complete search history.

(56) References Cited

U.S. PATENT DOCUMENTS

| 3,198,255 A | 8/1965 | Ownby |
| 4,578,991 A | 4/1986 | Nowlin |

(Continued)

FOREIGN PATENT DOCUMENTS

| EP | 2607621 A1 | 6/2013 |
| GB | 2309471 A | 7/1997 |

(Continued)

*Primary Examiner* — Allyson Trail
(74) *Attorney, Agent, or Firm* — Guerry L. Grune; ePatentManager.com

(57) ABSTRACT

A method, system, and associated apparatus are described for installing, inventorying, actuating, and/or accessing down-hole equipment in a wellbore. This comprises tagging a casing by inserting permanent components of material compositions within sections along the length of a casing. Inserted components and/or portions of an original section function as unique readable active and/or passive markers. The piping system is at least one pipe having a plurality of markers placed in radial sections strategically arranged with independently identical or different material compositions or embedded in a length of the wellbore casing. The sections function as markers forming a readable pattern readable by the reader(s). The reader is one of or a combination of any of the group consisting of a plug, a probe, a sensor, and/or a computer for reading markers. The reader travels in either a forward or backward direction.

40 Claims, 11 Drawing Sheets

(51) Int. Cl.
    *G01N 27/26*     (2006.01)
    *G01N 27/02*     (2006.01)
    *G01N 29/04*     (2006.01)
    *G01N 21/00*     (2006.01)
    *G01B 21/08*     (2006.01)
    *E21B 47/00*     (2012.01)
    *G01N 23/00*     (2006.01)

(56) References Cited

U.S. PATENT DOCUMENTS

| | | | |
|---|---|---|---|
| 4,703,279 | A | 10/1987 | Chapman et al. |
| 4,856,595 | A | 8/1989 | Upchurch |
| 5,331,318 | A | 7/1994 | Montgomery |
| 6,192,748 | B1 | 2/2001 | Miller |
| 6,373,248 | B1 | 4/2002 | Poitzsch et al. |
| 6,462,302 | B1 | 10/2002 | Grow |
| 6,598,682 | B2 | 7/2003 | Johnson et al. |
| 6,633,236 | B2 | 10/2003 | Vinegar et al. |
| 6,843,119 | B2 | 1/2005 | Patey et al. |
| 6,920,085 | B2 | 7/2005 | Finke et al. |
| 6,989,764 | B2 | 1/2006 | Thomeer et al. |
| 7,380,616 | B2 | 6/2008 | Virally et al. |
| 7,460,438 | B2 | 12/2008 | Hudson |
| 7,656,833 | B2 | 2/2010 | Chun |
| 7,958,715 | B2 | 7/2011 | Kinert et al. |
| 8,251,291 | B2 | 8/2012 | Sowers et al. |
| 8,276,674 | B2 | 10/2012 | Lopez de Cardenas et al. |
| 8,505,632 | B2 | 8/2013 | Guerrero et al. |
| 8,718,802 | B2 | 5/2014 | Boone |
| 2001/0050172 | A1 | 12/2001 | Tolman et al. |
| 2002/0093431 | A1 | 7/2002 | Zierolf |
| 2005/0194132 | A1 | 9/2005 | Dudley et al. |
| 2006/0283238 | A1 | 12/2006 | Sierra et al. |
| 2009/0120637 | A1 | 5/2009 | Kirkwood et al. |
| 2011/0297371 | A1 | 12/2011 | Church et al. |
| 2012/0085538 | A1 | 4/2012 | Guerrero et al. |
| 2013/0024030 | A1 | 1/2013 | Tubel et al. |
| 2013/0255963 | A1 | 10/2013 | Guerrero et al. |
| 2014/0076542 | A1 | 3/2014 | Whitsitt et al. |

FOREIGN PATENT DOCUMENTS

| | | |
|---|---|---|
| WO | 2005/001795 A2 | 1/2005 |
| WO | 2014035381 A1 | 3/2014 |

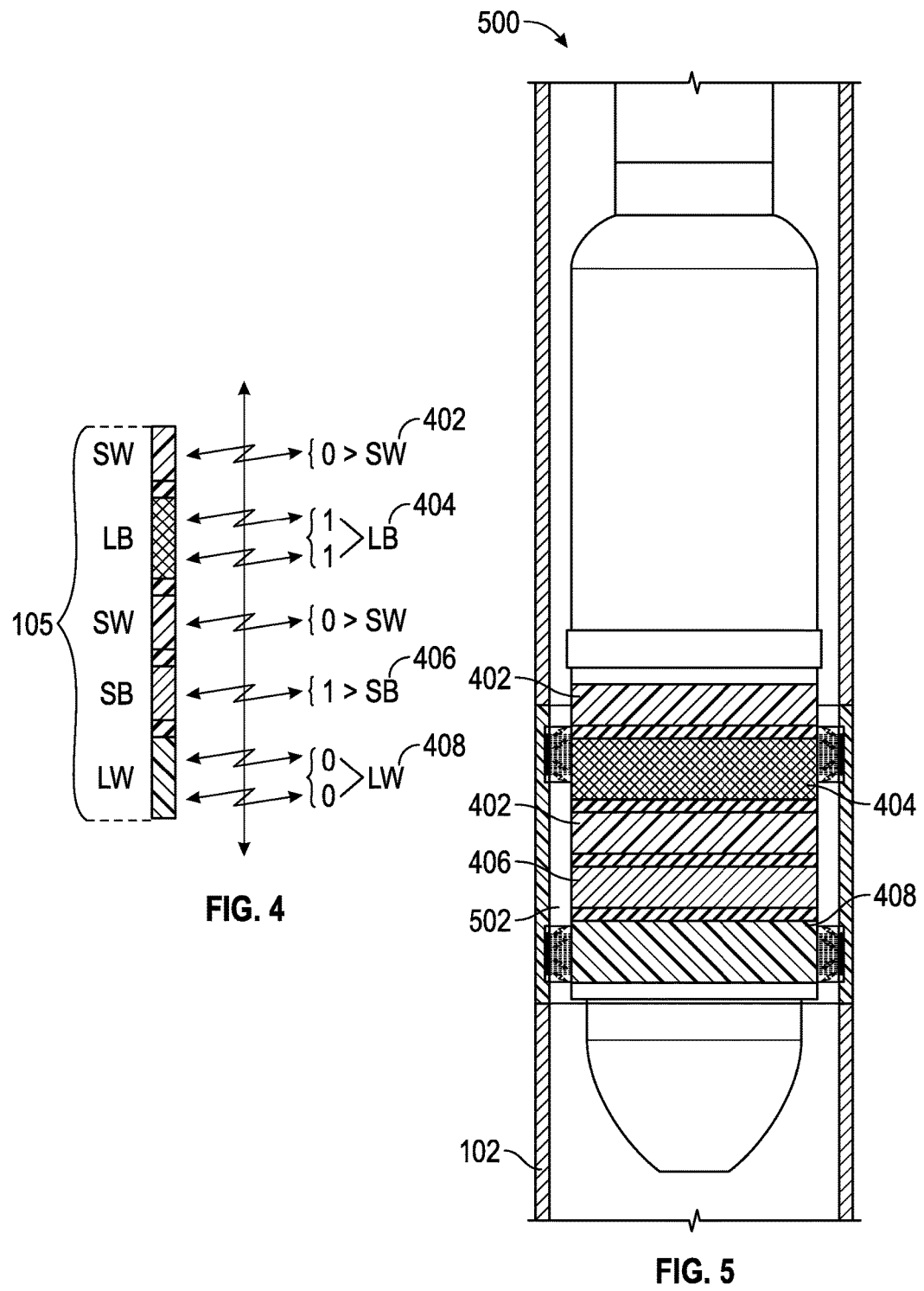

APPARATUS, METHOD, AND SYSTEM FOR IDENTIFYING, LOCATING, AND ACCESSING ADDRESSES OF A PIPING SYSTEM

PRIORITY

This application is a continuation of and claims priority under 35 USC 120 of Ser. No. 14/668,128 filed Mar. 25, 2015, entitled "Apparatus, Method, and System for Identifying, Locating and Accessing Addresses of a Piping System", which is a nonprovisional conversion of and claims priority under 35 USC 119 from Provisional Application No. 61/970,563 entitled "Apparatus, Method, and System for Identifying, Locating, and Accessing Addresses of a Piping System", filed Mar. 26, 2014, and Provisional Application No. 61/970,775 entitled "Location and Stimulation Methods and Apparatuses Utilizing Downhole Tools", also filed Mar. 26, 2014.

TECHNICAL FIELD

This invention relates to apparatus, methods, and systems used for locating and accessing addresses in one or more pipes. More specifically, the invention is directed to the drilling and completion of wells, such as hydrocarbon producing oil and gas wells. Most specifically, the invention involves locating specific addresses within these wells before, during, or after operating the wells.

BACKGROUND

Hydrocarbon fluids such as oil and natural gas are obtained from subterranean geologic formations (i.e., "reservoirs") by drilling wells that penetrate the hydrocarbon-bearing formations. Once a wellbore has been drilled, the well must be "completed" before hydrocarbons can be produced from the well. A well completion involves the design, selection, and installation of tubulars such as production tubing, drill pipes, landing nipples, gas lift mandrels, flow control devices, subsurface safety valves, packers, and collars with associated tools and equipment, such as perforation guns, that are located in the wellbore. The purpose of well completion is to convey, pump, and/or control the production or injection of fluids in the well. After the well has been completed, increased production of hydrocarbons in the form of oil and gas begins.

In many cases it is necessary to lower one piece of equipment into the well so that it can be installed, activated, inventoried, accessed, or otherwise manipulated according to a particular location in the wellbore (e.g., installing a gas lift valve in a particular gas lift mandrel when there may be several gas lift mandrels at different depths in the wellbore). Often it is necessary to perform a desired action at a desired location (e.g., a perforating gun that uses shaped charges to create holes in a well casing at a particular depth in the well).

In the past, rather complex methods have been used to determine when a given piece of downhole equipment is in the desired location in the wellbore. These methods are often imprecise, complex, and expensive.

There is a continued need for developing more intelligent and adaptable methods of drilling and completing oil and gas wells and for producing hydrocarbon containing fluids therefrom.

SUMMARY OF THE INVENTION

The present disclosure describes an apparatus, method, and system primarily designed for installing, inventorying, actuating, and/or accessing down-hole equipment in a wellbore. The method and apparatus comprises providing, first, a permanent structure such as a casing, collar, or other primarily cylindrical device, with an outer diameter that is smaller than the diameter of a borehole, to be inserted within the well bore. The present disclosure includes modifying the casing by using selected unique material compositions of pre-specified dimensions that reside inside and/or on an outer surface along a designated length of the casing. In this way, one or more patterns or sequences of patterns are developed along the casing providing a readable identification (ID) code. The identification (ID) code can be detected, received via transmission, and/or stored using appropriate devices. These patterns are created by strategically placing sections of materials of identical or differing composition(s) along both radial and axial sections (portions) of the casing. These selected materials can be conductive or non-conductive and collectively provide an ID code when used in combination with a reader.

More specifically the method involves installing, inventorying, actuating, and/or accessing down-hole equipment in a wellbore comprising;
 (i) marking a wellbore casing by inserting permanent components of selected material compositions within sections along a length of said casing within said wellbore, wherein said components and/or portions of an original section of said casing together function as unique readable active or passive markers,
 (ii) reading said markers, and;
 (iii) acting upon reading said markers using at least one reader.

The reader associated with both the method and apparatus, that completes one aspect of the system, is the use of any device including a probe, plug, sensor, code scanner, bar code scanner and/or computer that searches, acquires, senses, analyzes, stores, manipulates, and/or redirects data acquired from the casing. In other words, the reader device must be capable of distinguishing changes in the strategic placement of the different material compositional sections, and the associated material properties that are placed in or on these sections along the length of the casing, pipe, or piping system.

The method includes inserting markers in strategically placed locations along an axial and/or radial portion of the casing creating one or more patterns or sequence of patterns wherein the markers are comprised of components each possessing, independently, identical or different selected material compositions with corresponding cross sectional areas. The material compositions may be solid conductive or non-conductive metals, wire and/or screening metals, and/or polymers that may or may not be filled with conductive and/or magnetic fillers. In one embodiment, these sections are often conductive or non-conductive radial rings, comprised of independently the same or different materials and changeable dimensions along both the radial and axial direction of a collar. These rings also function as markers in that the insulative or conductive (or at least semi-conductive) alternating material properties along the continuous length of the collar provide the ability for the reader to read specific addresses. The pipes and piping systems may be used for purposes other than oil and gas well completion. In one configuration, at least two or more of the components are conductive rings which, when energized, comprise active markers, that together with passive markers along the length of the casing, individually or collectively function by providing a readable identification (ID) code created when one or more patterns or sequence of patterns are read by the reader. The readable identification (ID) code obtained from the patterns provides the ability to determine precise locations along a specific length of the casing. These locations are specific addresses that correspond with a detectable feature at the surface of, or embedded in, the casing. By providing the readable ID code in this manner, the markers can appear as multiple patterned readable bars to a reader that is reading, (in some cases by scanning), the permanent markers (sectional components) of the casing. These bars can be read as distinct spatial codes, distinct binary codes, and/or arranged to be read as bar codes.

Reading by scanning or otherwise acquiring and detecting the spatial, binary, and/or bar code with at least one reader, enables finding the exact address along the length of the casing. The casing is often a production collar within a borehole.

For this method the casing can be a production collar, and the at least one reader is at least one probe wherein the probe is an autonomous tool (functioning on its own and in some cases being preprogrammed). The reader can also be one or more tethered probes wherein at least one probe functions alone or in any combination as a plug, sensor, computer, recorder, detector, scanner, and/or barcode scanner. The at least one probe detects material property differences within the permanent components within the sections (or portions of the sections) along the length of the casing. The materials of composition and/or said markers can have discontinuities in material properties including electrically conductive materials with non-conductive gaps.

In yet another embodiment, the reader(s), as alluded to above, are substantially autonomous tools such as a probe. The probe functions singularly, collectively (there may be multiple probes) or in any combination as a sensor, computer with or without storage memory, recorder, scanner, and/or barcode scanner. Reading by the probe(s) occurs via transmitting, computing, recording, receiving, storing, distinguishing and/or measuring, at least a portion of data received by the probe or exchanged between multiple probes, as needed. Data signals can be actively or passively transmitted from the casing. The probe can be moving or stationary and the data signals are read while the probe is moving or stationary. Likewise, the collar and/or casing may be moving or stationary. In this embodiment, the casing itself can be acting as a probe and the casing could be moving or stationary. The probe could also be moving or stationary separately or in concert with the casing. Signals are read while the probe (or casing/collar) is moving or stationary.

In an additional embodiment, the at least one probe functions as a sensor that senses changes in permanent components of selected material compositions along a length of the casing. This method is used when permanent marking of the casing is desired. Here again the casing could be a production collar installed in the wellbore. Permanent components are placed as radial sections in and along the length of the casing. Marking of the casing is accomplished before or during the casing installation, and/or marking is in production collars being installed in the wellbore. The probe acting as a sensor provides readable (ID) code that identifies specific collar features. More specifically, providing the readable ID code to a reader is one method for identifying specific collar mechanisms. Even more specifically, providing the readable ID code to a reader is another method for identifying branching of a borehole collar. In all cases, the readable ID code is being read by the reader and the reader can be stationary or moving. The code can also be read while the reader is moving in either a forward or backward direction. To ensure the overall code can be read in both directions, the code is normally provided with both a leader code and a trailer code. This distinguishes not only precise addresses (locations), but also the direction and location associated with the code.

Readable ID code to the probe (or any reader) assists in identifying specific borehole features. Providing the readable ID code to a reader assists in identifying specific casing mechanisms (such as valves). Providing the readable ID code can assist in identifying branching of a borehole casing. The readable ID code can be read by the reader when it is moving in either a forward or backward direction. The readable ID code can be read by a reader, which is tubing conveyed, on a wireline, or independently propelled, so that the code is translated into data, wherein the data is sent to an uphole surface of a wellbore. The readable ID code can be conveyed uphole to the surface by sending data from the code obtained to the uphole surface.

It is also possible to provide readable ID code read by a reader wherein the reader is not connected to the uphole surface. In this case, the readable ID code is read by a reader connected to equipment not limited to measuring, computing, recording and/or actuating. The readable ID code is read by a reader moved by fluids in the wellbore and not limited to fluids for pumping and production. In one of yet another set of embodiments, the readable ID code is read by at least one reader moved by gravity, moved by buoyancy in the fluid, moved by self propulsion, or any combination of these methods, during use within the well. In an alternative embodiment, the readable ID code is read by a reader moved by self propulsion.

For the methods described above, the reader (probe or other devices) has the ability to take action upon reading readable ID code. This action can include; releasing mechanical keys, actuating an electrical, magnetic, electromagnetic, pneumatic, hydraulic, fiber optic device or other communications circuit, and/or initiating measurements of these devices or circuits before, during, or after well completion. In many cases, these measurements are regarding the collar, borehole, as well as sections and portions of sections along the length of the piping.

The action upon reading readable ID code can be communicating with equipment along a length of the casing. Actuating communications can be accomplished autonomously by the probe, or remotely using communications to the equipment at the surface of the borehole.

An additional embodiment includes a piping system comprising; at least one pipe having sections strategically arranged so that the sections comprise independently identical or different material compositions along a surface or embedded in, a length of said pipe, wherein a plurality of passive and active distinguishable markers are placed in the sections forming a readable pattern or sequence of patterns that is read by at least one reader, thereby locating specific addresses along the length of the pipe.

In yet another embodiment, at least one device is comprised of a unit for reading markers along a length of a piping system that reads strategically arranged sections of at least one pipe where the sections comprise independently identical or different material compositions along a surface or embedded in, a length of the pipe, and wherein markers are placed on or in the sections so that the markers form a readable pattern or sequence of patterns that are read by the unit thereby providing data and specific addresses along the length of the pipe.

In another embodiment, at least one device is comprised of sections in at least one pipe strategically arranged so that the sections comprise independently identical or different material compositions along an inner surface, an outer surface, or between inner and outer surface along a length of pipe, so that the sections themselves form a distinguishable readable pattern or sequence of patterns that are read by at least one reader.

In a further embodiment, at least one pipe comprises a plurality of passive and active markers placed in sections strategically arranged so that sections comprise independently identical or different material compositions along a surface or embedded in, a length of pipe, so that markers form a readable pattern or sequence of patterns readable by at least one reader.

BRIEF DESCRIPTION OF THE DRAWINGS

FIG. 4 is a visual display of the readable identification (ID) code of a coded casing and associated digital signals obtained during reading.

FIG. 5 is a schematic representation of an alternate embodiment depicting a casing with sensors using a coded probe.

DETAILED DESCRIPTION

Figure 1A:
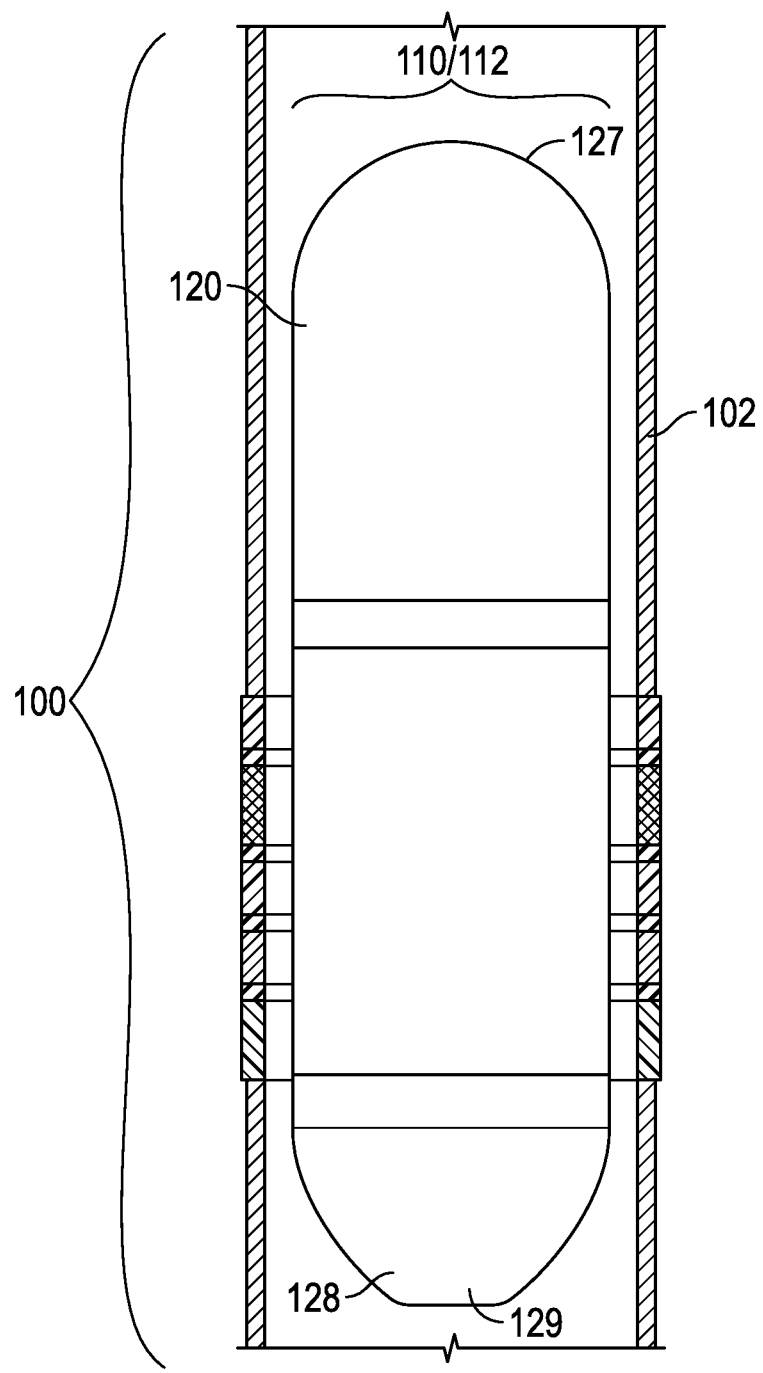
FIG. 1A is a schematic drawing of a completed assembly of an untethered probe that is fully housed in a smooth enclosure.

As summarized above, one embodiment of the present invention is a method of installing, inventorying, actuating, and/or accessing down-hole equipment in a wellbore comprising;
(i) marking a wellbore casing by inserting permanent components of selected material compositions within sections along a length of said casing within said wellbore, wherein said components and/or portions of an original section of said casing together function as unique readable active or passive markers,
(ii) reading said markers, and;
(iii) acting upon reading said markers using at least one reader.

I. Providing a Coded Casing

In this embodiment, the method (and overall system) involves inserting markers in strategically placed sections of the pipe, so that patterns or sequences of patterns are created along and within an (axial and/or radial) portion of a pipe, piping system, collar, or casing. Markers are comprised of (in most cases radial) sections each possessing, independently, identical or different selected material compositions that are either on the surface or embedded within cross sectional sections of the casing. In one embodiment, the casing provides two or more sections (or rings inserted into the casing) that are; conductive and/or non-magnetic, non-conductive and/or magnetic, or non-conductive and/or non-magnetic. Using these sections (rings) collectively along the length of the casing creates the basis of a readable identification (ID) code. The code corresponds with one or more specific patterns due to the insertion of different material compositions in the casing, which allows for distinguishing the markers. The different material compositions, exhibit contrasting resistivity values along the length of the casing. By inserting these different sections (and/or markers) into the casing (in some cases sections of the rings are composed of different materials), a basis is formed for determining discrete locations that are specific addresses based upon reading the ID code. The addresses are read and correspond to code that exists as portions of the casing. These casing sections and associated portions are either conductive, non-conductive, semi-conductive, magnetic, non-magnetic, radioactive, non-radioactive, energized and/or non-energized, resulting in readable patterns or sequences of patterns.

Collectively, the sections, with or without markers, are placed along the casing (or collar). Rings (acting as markers), with varying thicknesses and widths, can be inserted directly into sections of the casing and thereby provide readable pre-addressed ID code that corresponds to a precise address in the casing. In this manner, the pre-addressed ID code can be developed as either a type of passive or active "casing code". How the code is detected, received, and/or transmitted is dependent on which materials are used for each section of the casing (or the types of rings used and their placement). The casing sections or the rings or both may be "doped" with additional elements that can be read (detected) by the reader. In this case "doping" is intended to mean adding specific features to the overall material compositions that can be activated or that can be easily detected. Detectable properties and associated property values and/or signals can be emanated, transmitted, absorbed, and/or reflected and then read from materials requiring no doping (such as magnetic or conductive materials) as well as from doped materials.

It is possible to embed, by doping or other methods, specific materials in the casing and/or markers. It is also possible to insert electrical, mechanical, magnetic, electromagnetic, and/or optical circuits or corollary circuitry into these specific materials. The types of embedded circuits for example may include active or passive resonant circuits, transformers, analog or digital transponders. The detectable properties and/or signals can be detected by distinguishing some aspect of a material property including magnetic fields and resulting magnetic eddies, from sensors, and/or from (frequently programmed) circuitry. In all cases, the overall material composition of the rings and/or other sections of the casing are different and these detectable, readable differences, provide patterns or a sequence of patterns.

Sections (or portions of sections) of the casing which are non-conductive and/or are void of circuitry will not emit or emanate signals. Instead, these "passive" non-energized sections of the casing also have detectable properties (e.g. resistivity, conductivity and/or magnetism), which when used to provide a basis for distinguishable code, assist in locating other addresses. The addresses, based upon the casing properties that are detected, are found when a specific length of the casing (with or without markers) provides a fully developed code along that specific length. In this manner, the entire casing (or collar) can be logged (mapped). This allows the casing to act as a "passive code providing" device. In order to read this code, at least one code reader, such as a probe, must be employed. The reader will also be selected to be active or passive, depending on the properties of the casing.

It must be emphasized, that a key aspect of the present invention is that the casing (or pipe or pipeline or collar) within the borehole, is permanent. This allows for the creation of a robust and extremely long lived (in comparison with any other systems) wellbore address locator that functions during the entire life of the wellbore. As previously stated, the readable identification (ID) code provides the reader or user or both, with the ability to determine precise locations along a length of the casing. These locations are specific addresses that correspond with a detectable feature at the surface of, or embedded in, the casing. By providing the readable ID code in a permanent manner, the markers can appear as multiple patterned readable bars to a reader that is reading, (in some cases by scanning), the permanent markers (sectional components) of the casing. Taken in total (collectively), the bar codes are permanent identification (ID) codes which when read by a single probe (or multiple probes) are capable of providing positional and overall compositional make-up of specific local addresses along the casing. In this manner, the casing is fully "logged" and the wellbore is completed with a "signature" that allows acting with precision within the wellbore, where and when needed. In order to ensure meeting these requirements additional embodiments of the present invention exist.

II. Providing an Active Reader for Reading the Coded Casing

In all cases described, the reader can be a probe, a scanner, a bar code scanner, a computer, a detector, a transmitter and/or a receiver that travels inside the coded casing described above. In one instance, a data signal is emitted by a reader—in this case a probe—and sent to the casing for reading the code. The signal is subsequently "reflected" and received by the same or a different probe or set of probes, yielding at least position and material composition dependent data obtained from the coded casing.

In a special set of embodiments that is diagrammed schematically in FIGS. 1-4 described herewithin, the casing has to least one permanent identification (ID) codes using materials which exhibit different responses to eddy current measurement. The probe measures the eddy current effect in the casing and the permanent identification (ID) codes.

The eddy current effect is well understood by those trained in the art, but is described more fully as follows: the probe emits energy which can be detected and invokes a response from the coded casing. In this case the probe emits electromagnetic radiation resulting in eddy currents in the coded casing, which are measured by eddy current sensors, as the energized probe travels along the length of the casing (or collar). The probe could also function as a receiver to receive signals from the casing (described in more detail below). Different material compositions in the coded casing exhibit different resistivity values. Copper, for instance, is a good conductor of electricity but is non-magnetic and exhibits a low resistivity, in comparison with steel. Steel exhibits a higher resistivity than copper but is magnetic. Plastics are neither conductive nor magnetic unless filled or otherwise treated with conductive and/or magnetic elements.

In this embodiment, the resistivity differences due to the varying material compositional sections (which may be markers) along the length of the casing, are determined by non-contact eddy current measurement techniques. As a result of sending a small amount of current (mA) into an eddy current sensor, a magnetic field and associated eddy current is induced. Most specifically, at least one ring shaped eddy current sensor and underlying eddy current ring shaped shield is placed either on the surface or embedded within the probe. This combination masks the sensing of eddy currents inside the probe. This technique ensures that there is no interference in the measurement of either the magnetic field or resultant eddy current due to the presence of the probe. The shields are optional, but preferred.

Without this shielding on the probe, the ability to perform the desired measurements of eddy currents in the coded casing would be greatly diminished. The eddy current shield underlying the eddy current sensor results in directing the sensitivity of the sensor in a radial direction away from the probe and therefore toward the casing. This technique ensures that the sensor preferentially measures, almost exclusively, resistivity differences existing in the various material compositional sections (or markers or both) along the length of the casing.

The probe associated with this system also functions as a reader of the coded casing. The coded casing is read by sensing (as the probe is traveling in either direction and at times stationary within the casing) markers that correspond with the equivalent of bars having differing widths formed by "seeing" portions of rings embedded along the length of the casing. These patterns collectively, when read, provide casing codes. Collectively, these bars make-up the patterns that essentially are the same as a bar code. The probe, therefore, in this case, serves at least two functions; reading casing code and providing eddy current sensor(s) that measure resistance of the different material compositions in the casing. The measurements depend on the probe's location with respect to specific sections (markers, rings, etc.) within and along the coded casing.

By inserting into the casing at least one marker (ring) made with materials exhibiting a low resistivity but no magnetic permeability (i.e. copper or silver) and another marker (ring) with materials exhibiting a high resistivity and high magnetic permeability (i.e. ferrite) it is possible to distinguish these markers (either in the form of rings or as sections of the casing itself) from one another, by comparing eddy current values using the eddy current sensors carried by the probe.

Another function of the markers (rings) is to shield the (metallic) casing from being measured by the eddy current sensor (thereby masking the casing). To ensure full shielding of the casing occurs, in the case of the low resistivity but non-magnetic permeability ring (i.e. copper or silver), the material must be significantly thicker than the skin effect utilized by the eddy current sensor. In the case of the markers (rings) exhibiting a high resistivity and high magnetic permeability (i.e. ferrite), the induced magnetic field providing the eddy current sensor never reaches the metallic casing.

Most specifically, in developing the probe and associated passive code generating device (i.e., the casing, etc.), it is important to generate "clean" signals. Here, the word "clean" refers to signals that are mostly free from or easily contrasted with background noise, are easily detectable, are determined to be from an exact and specific source, are clearly resolved, and if necessary, amplified. These signals provide a method for the probe to act or react as needed and in some cases, the signals may be sent uphole for a user to interpret.

By utilizing both a probe and coded casing as described, an uninterrupted, unimpaired, easily detected material property change in the markers (rings) is accomplished using easily detected changes in eddy current values received from the coded casing on a permanent basis.

Additionally, the probe may be moving or stationary and includes several features that allow for ease of travel within the fluid regions confined within the casing (or collar) residing in the borehole. These features include geometry constraints such as pointed or rounded mechanical portions of the probe at one or both ends. The probe must be water and pressure resistant and as "leak proof" as possible to withstand harsh pressure and temperature downhole conditions during operation. In addition, the probe can also include some form of random access memory (RAM) included with a computing device (computer) and with electronics powered by a power source, such as a battery.

The combination code-and-reader system is shown in FIGS. 1A-1E. FIG. 1A is a schematic representation of one type of a code-and-reader system [100], with a casing [102] shown to contain a probe [110] having an outer portion (surface) [120], a conical terminus [128] with an optional access point [129] for a connector (not shown) and an upper end probe portion [127]. The probe [110] depicted in FIG. 1A is an example of an untethered probe [112] having a rounded upper end probe portion [127]. The outer portion (surface) [120] is smooth and void of external features so that there is no interference with the motion of the probe [110] or in communicating with the probe [110] while in the casing [102].

Figure 1B:
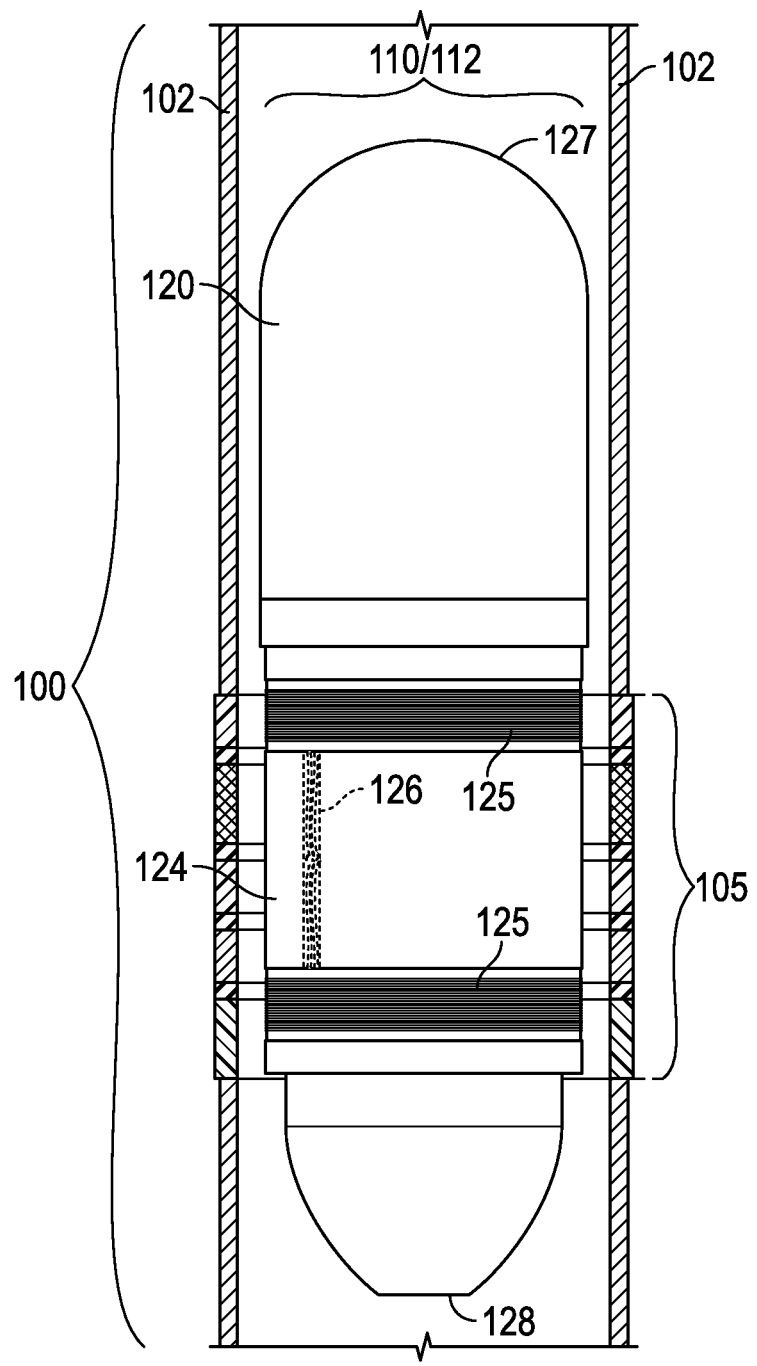
FIG. 1B is a schematic depicting an untethered probe within a casing with a top half of the probe having an outer surface covering and a lower half having the outer surface removed so that the coiled sensors can be viewed. The probe is depicted to be within a coded casing.

FIG. 1B is also a code-and-reader system [100], with a casing [102] that has different material sections functioning to provide a coded region (set of rings) within the casing [105] The casing houses a probe [110] having an outer probe portion (surface) [120], a conical terminus [128] with optional access [129] for a connector (not shown), an upper end probe portion [127], sensor coil(s) [125] which extend along the circumferential surface of the foil shielding [124] of the probe [110] and are connected via a wiring bundle for sensor coils [126]. The probe [110] depicted in FIG. 1B is an example of an untethered probe [112] having a rounded upper end probe portion [127], thus providing an autonomous probe capable of operating without further mechanical direction.

The coded region of the casing [105] is constructed from different material sections positioned along the casing [102] in such a manner as to provide "readable" variations in the casing [102] creating a coded casing with an exact address. The sensor coil(s) [125], when energized provide sensing capability to interpret the code from the coded region of the casing [105].

Figure 1C:
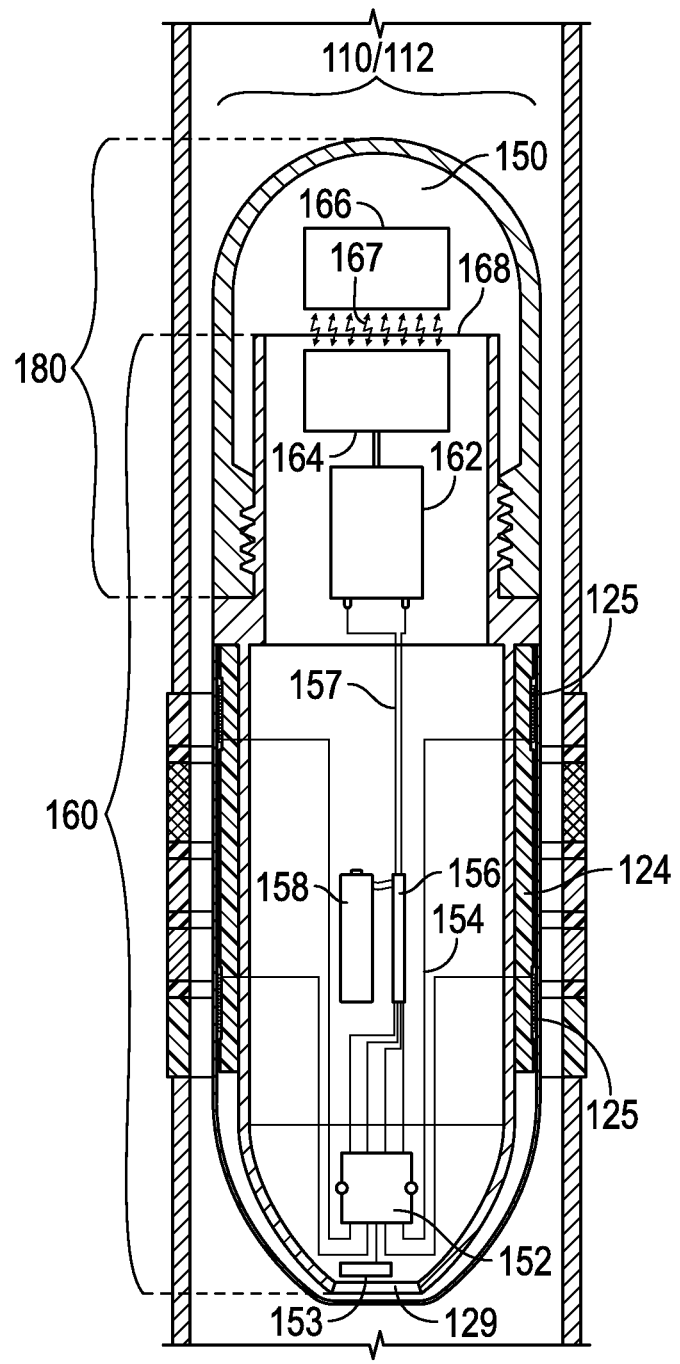
FIG. 1C is a cross-sectional schematic view of the internal portion of an untethered probe with a rounded end. The probe is depicted to be inserted within a coded casing.

FIG. 1C is a cross-sectional area depicting the untethered probe [112] version of the code-and-reader system [100] of FIG. 1B. The inner cross-sectional portion of the probe [150] provides the probe [110], in an untethered probe [112] version, with a pressure vessel [160] component and a female jacketed upper end [180] component (shown as rounded). The female jacketed upper end portion [180] of the probe [110] holds mechanical components which can operate at normal well bore pressures.

The power supply unit [158] provides energy to the components of the probe [110] via an electrical wiring system. Energy is distributed to the electronic sensor and control board [156] in order to energize the motor and shaft [162] for the rotating of the magnetic couplings, provided as an inner portion of the rotating magnetic coupling [164] and the outer portion of the rotating magnetic coupling [166]. With reference to the inner and outer portion of the rotating magnetic couplings [164,166], "inner" refers to the portion of the rotating magnetic coupling that is inside the pressure vessel [160] and "outer" refers to the portion of the rotating magnetic coupling that is outside the pressure vessel [160]. The coupling can also be comprised of permanent magnets.

The magnetic coupling [164,166] operates using the motor and shaft [162] and provides a magnetic field [167], which couples the torque of the motor [162] through the magnetic coupling seal [168] to the outer magnetic coupling [166]. This coupling ensures that the seal of the pressure vessel [160] protects the internal elements within the pressure vessel [160].

Figure 3A:
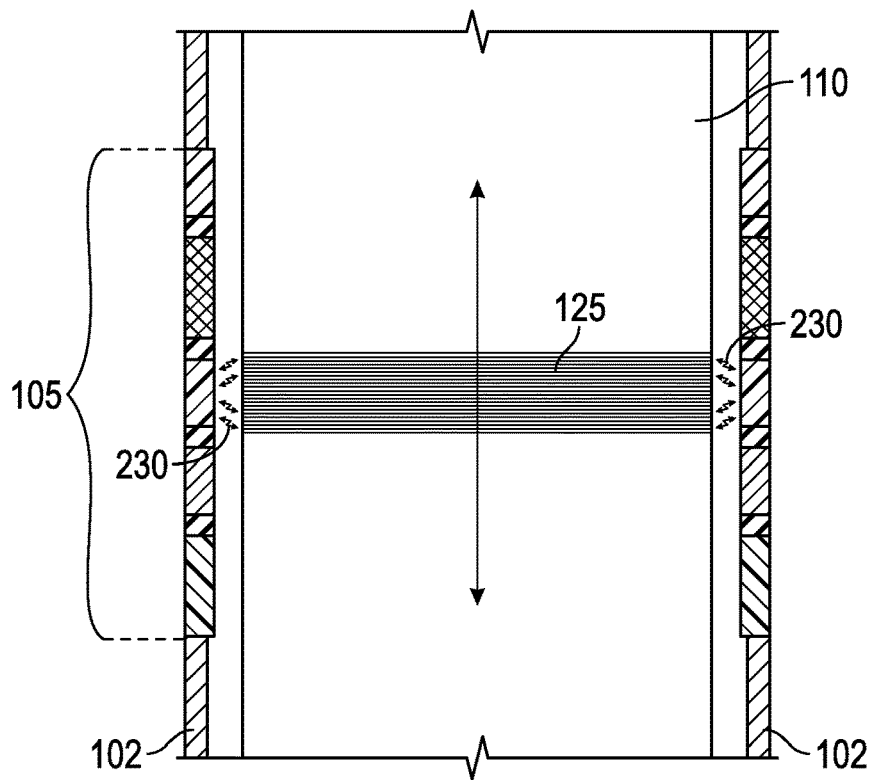
FIG. 3A is a schematic depiction of a cross-sectional portion of a coded casing and a portion of a probe with a single coiled sensor.

The pressure bulkhead [152] is an electrical feed-through that serves as a junction for the wiring system and also energizes the probe [110]. It is housed in the conical terminus [128] of the probe [110]. Wiring from the pressure bulkhead [152] extends to the outer probe portion (surface) [120] and along the circumferential surface of the foil shielding [124] of the probe [110], thereby creating the sensor coil(s) [125]. An accelerometer [153] is shown and can be wired to the pressure bulkhead [152]. The accelerometer [153] is essential for a single sensor coil probe (as shown in FIG. 3A) so that the measurement of velocity of the probe can be obtained.

Figure 1D:
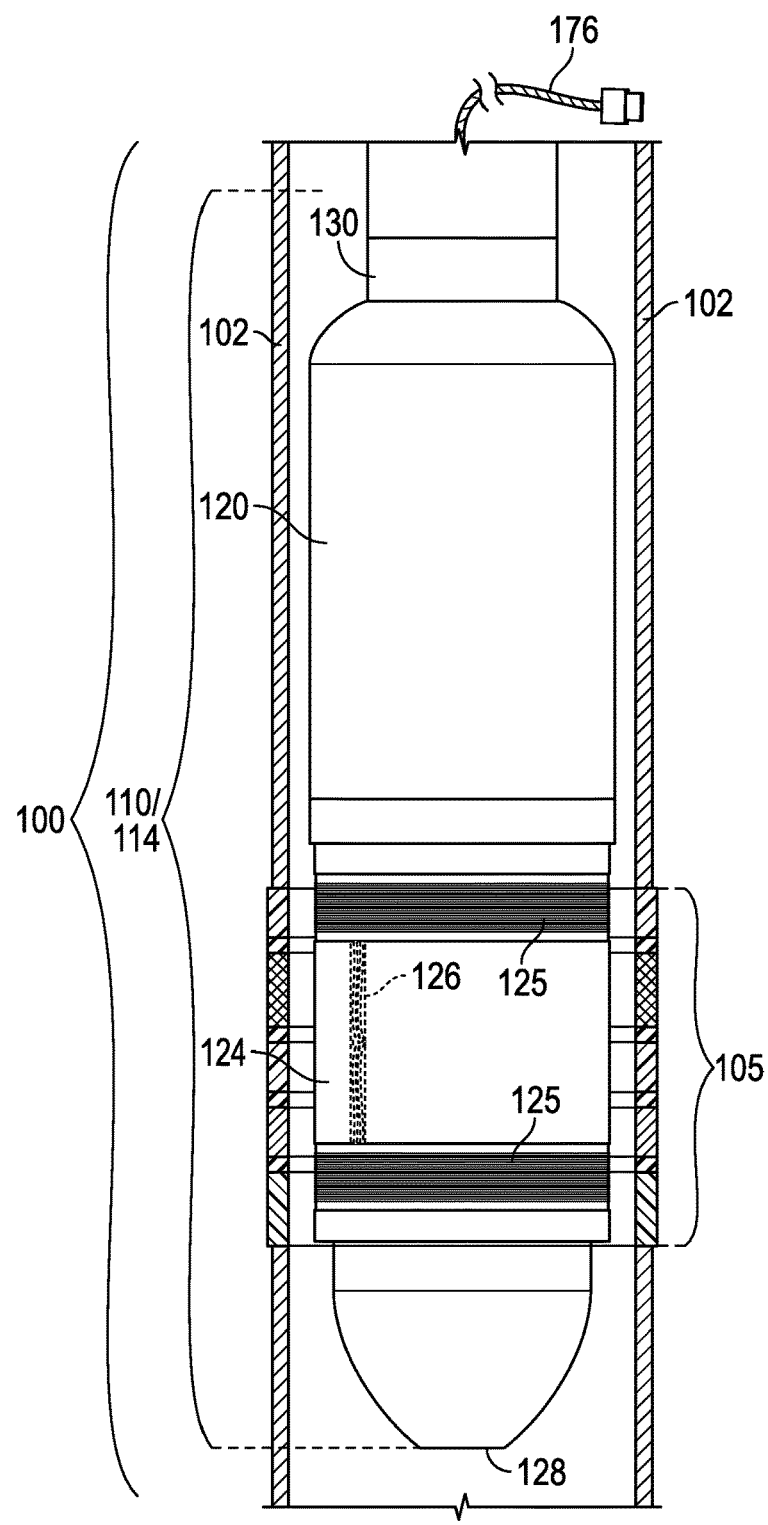
FIG. 1D is a schematic depicting the external surface of a tethered probe with a tapered end residing within a cross-section of a coded casing.

FIG. 1D is a code-and-reader system [100], with a casing [102] using different material sections, provides a coded region of the casing [105], housing a probe [110] having an outer probe portion (surface) [120], a conical terminus [128] with optional access [129] for a connector, an upper end probe portion [127], and sensor coil(s) [125] which extend along the circumferential surface over the foil shielding [124] of the probe [110]. The sensor coils [125] are connected via a wiring bundle for the sensor coil(s) [126]. The probe depicted in FIG. 1D is an example of a tethered probe [114] having a tapered upper end probe portion [130] and an uphole tether [176] capable of communication and mechanical attachment with the probe.

Figure 1E:
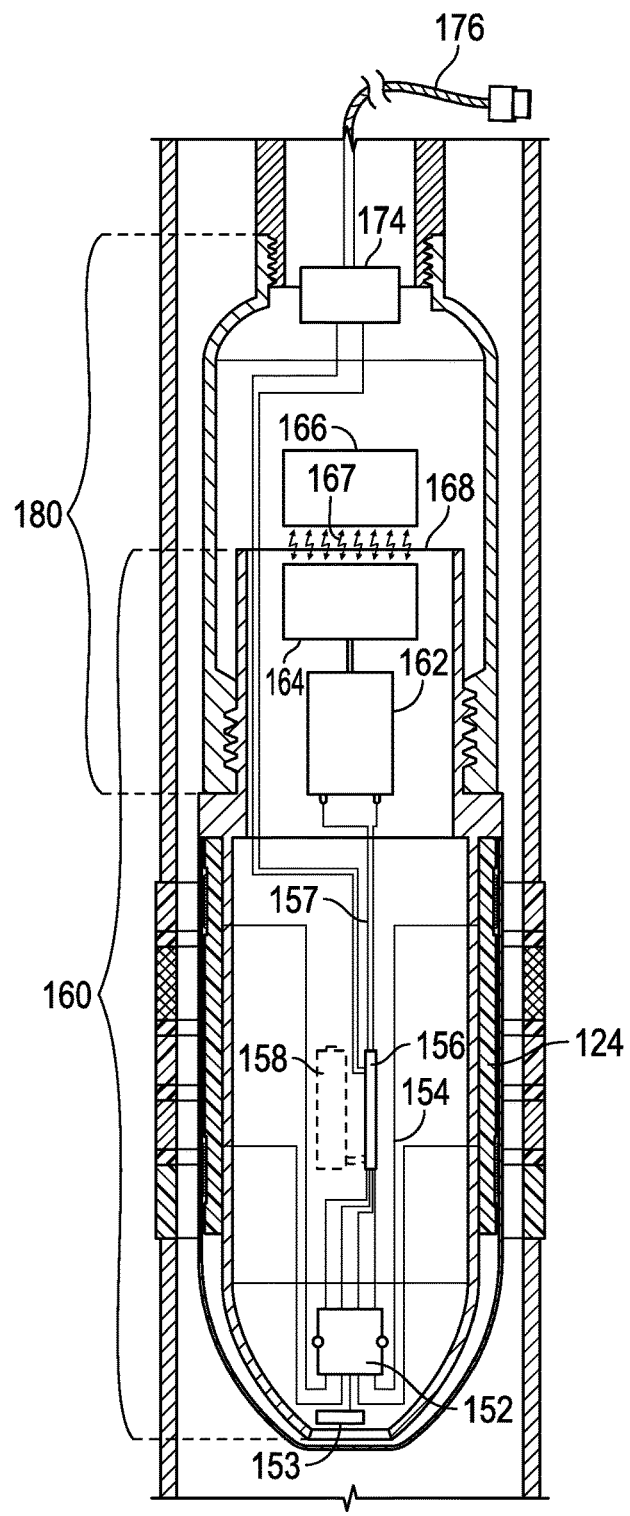
FIG. 1E is a schematic of a cross-sectional internal portion of a tethered probe with a tapered end, including bulkhead and electrical components. The probe is depicted to be within a coded casing.

FIG. 1E is a cross-sectional illustration of the tethered probe [114] version of the code-and-reader system [100] of FIG. 1D. The inner cross-sectional portion of the probe [150] provides a pressure vessel [160] component and a female jacketed upper end portion [180] component (shown as a tapered section). The casing of the pressure vessel [160] component is threaded (or otherwise attached) together with the female jacketed upper end portion [180] of the probe [110] to maintain a sealed system at atmospheric pressure ($P_{ATM}$).

The power supply unit [158] provides energy to the components of the probe [110] via an electrical wiring system. An alternative embodiment of the invention is that energy is provided via an uphole power supply to the downhole components of the probe [110] via an electrical wiring system through an electrical connector [174] to an uphole tether [176]. Energy is distributed to the electronic sensor and control board [156] in order to energize the motor and shaft [162] for rotating of the magnetic couplings. These couplings are shown as an inner portion of the rotating magnetic coupling [164] and an outer portion of the rotating magnetic coupling [166].

Rotation of the magnetic couplings [164,166] by the motor and shaft [162] creates an induced magnetic field [167] (also able to be provided through the use of an alternative permanent magnet arrangement) which ensures sealing, with the optional seal cup [168] the pressure vessel [160] component and the female jacketed upper end portion [180] to maintain safe operation of the internal elements of the pressure vessel [160].

Figure 2A:
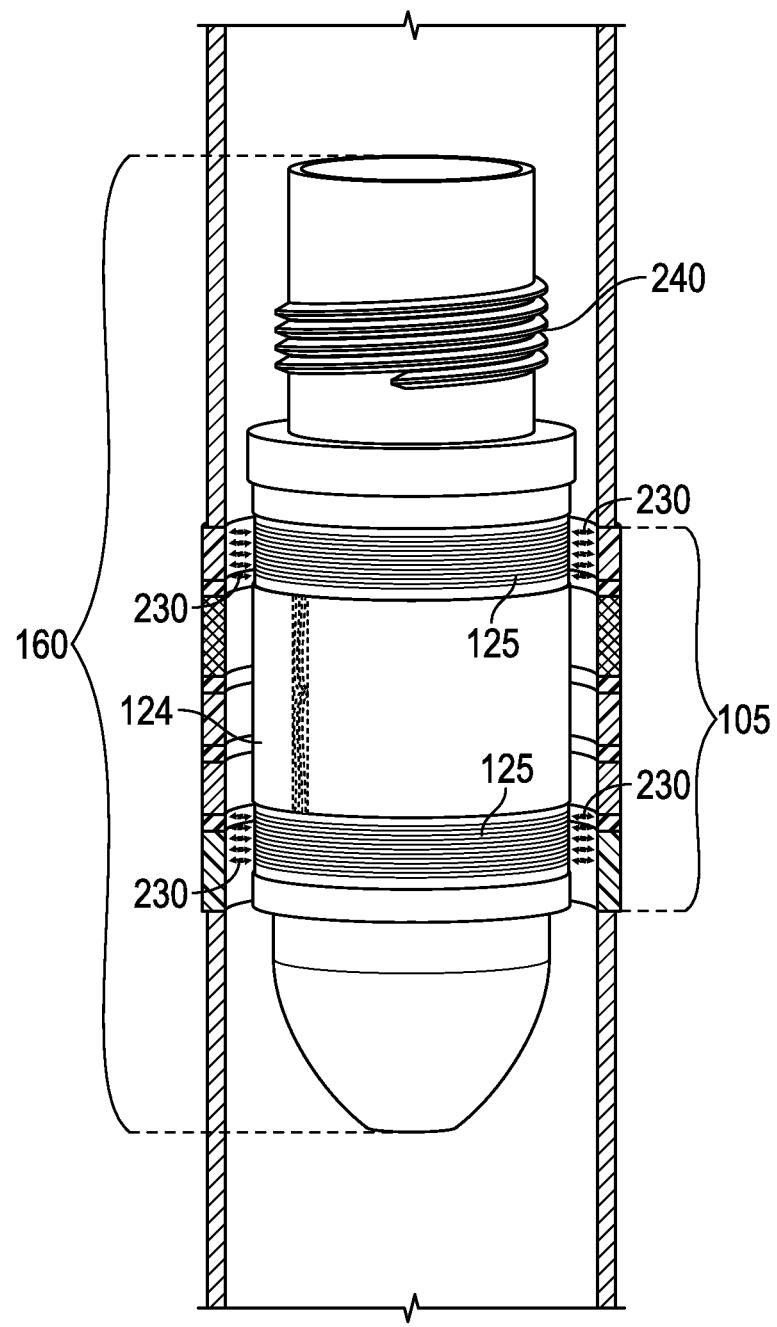
FIG. 2A illustrates a portion of a probe with a threaded male adapter.

The pressure bulkhead [152] is an optional electrical feed-through that serves as a junction for the wiring system that energizes the probe [110], and is housed in the conical terminus [128] of the probe [110]. Wiring from the pressure bulkhead [152] follows to the outer probe portion (surface) [120] extending along the circumferential surface of the foil shielding [124] of the probe [110] and creates the sensor coil(s) [125]. An accelerometer [153], is shown as wired to the pressure bulkhead [152], and is an optional component for a dual sensor coil probe as shown but required as sated above for a single sensor coil probe, FIG. 2A is an outer surface schematic of the pressure vessel [160] component of the probe [110] (not fully featured), with the tapered threaded male adaptor portion [240]. Eddy currents [230] generated by energizing the sensor coil(s) [125] allows for receiving a response from the coded region of the casing [105] are shown.

Figure 2B:
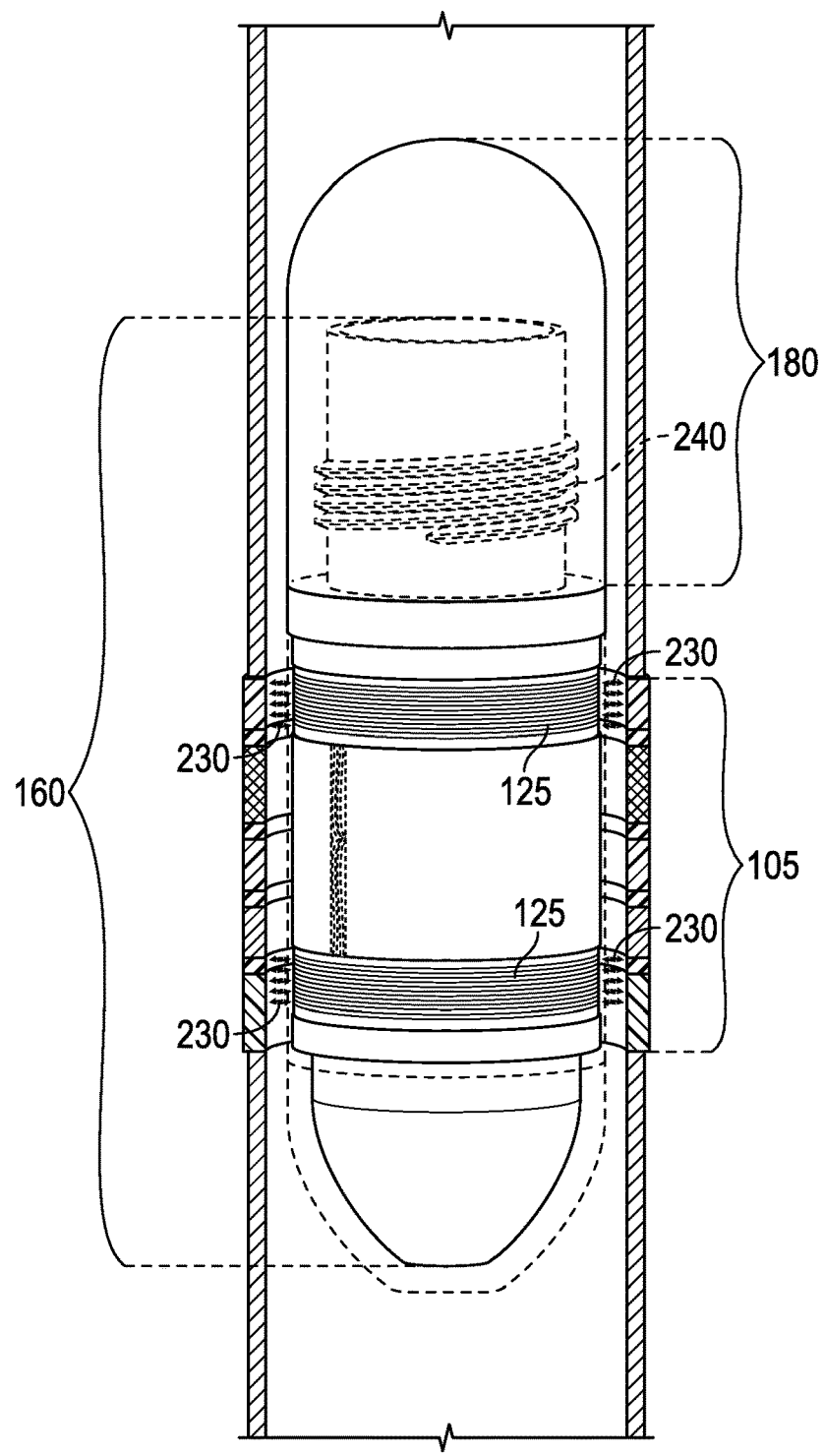
FIG. 2B illustrates an untethered probe with a female jacketed upper end.

FIG. 2B is an outer surface schematic of the pressure vessel [160] component of the probe [110] (not fully featured), with the tapered threaded male adaptor portion [240] completed by being connected with a female jacketed upper end portion [180] component-shown as untethered and rounded. Eddy currents [230] are shown which are generated by energizing the sensor coil(s) [125] and allows for receiving a response to the coded region of the casing [105].

Figure 2C:
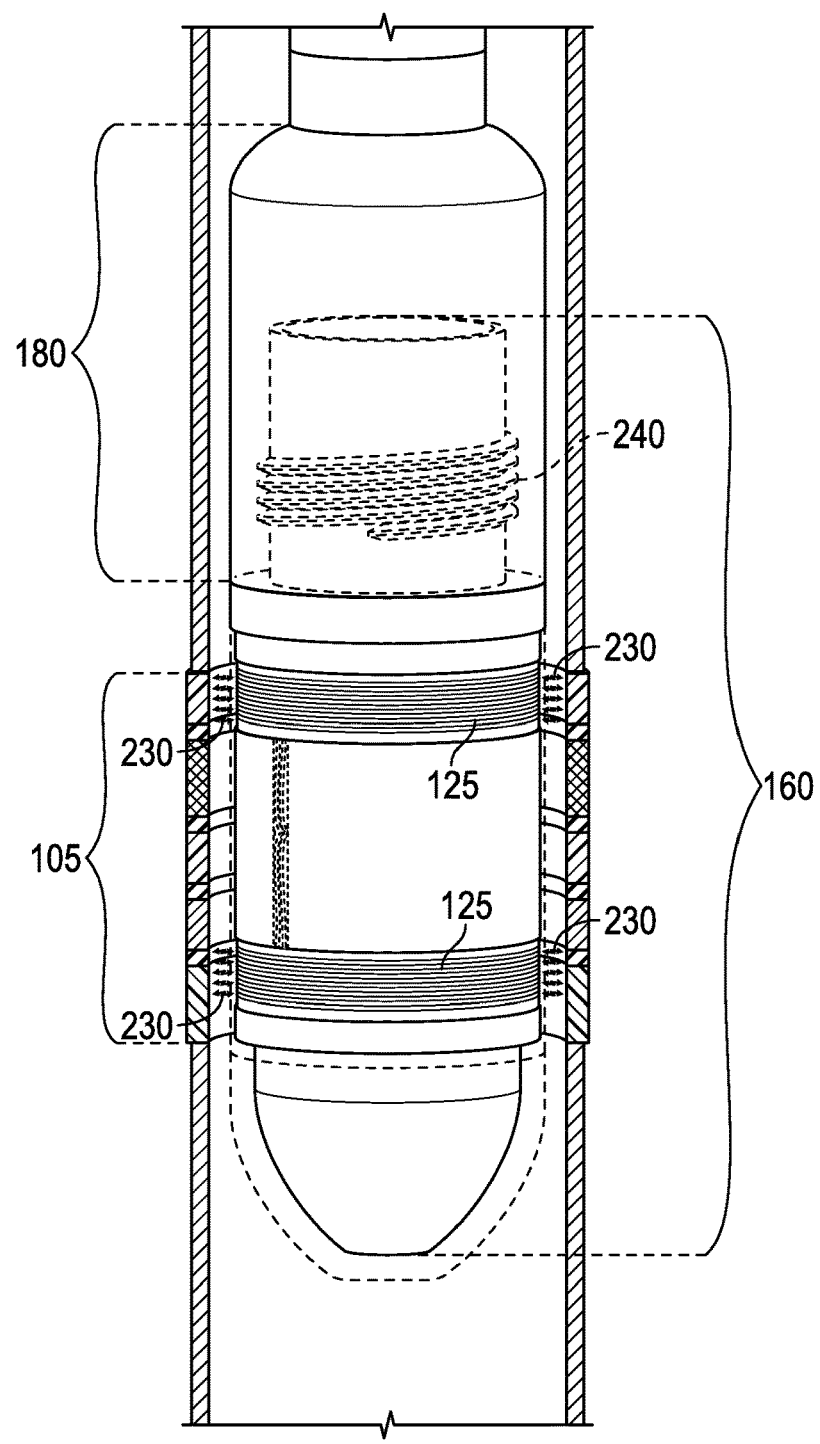
FIG. 2C illustrates a tethered probe with a female jacketed covered upper end.

FIG. 2C is an outer surface schematic of the pressure vessel [160] component of the probe [110] (not fully featured), having a tapered threaded male adaptor portion [240] completed by being connected with a female jacketed upper end portion [180] component—shown as tethered and tapered. Eddy currents [230] generated by energizing the sensor coil(s) [125] allows for receiving a response to the coded region of the casing [105].

FIG. 3A is a cross-sectional portion of the casing [102] exhibiting a coded region of the casing [105], where forward or backward, uphole or downhole movement of the probe [110] allows for the sensing direction and specific addresses by the sensor coil(s) [125]. The sensors sense the coded region of the casing [105]. An accelerometer [153] is added to the probe here as a single coiled sensor and is capable of measuring the code width if it travels at a generally constant speed. In this case, time is a factor in calculating the bar width which are determined by the probe reading variable lengths of the coded casing. By adding an accelerometer [153], changes in speed can be determined (if acceleration is known, speed can be calculated). By knowing the change in acceleration, the actual speed of the probe can be judged and thereby greatly diminish the effect of changes that the speed of the probe has on the quality of the readings of the ID code. As acceleration reaches zero and reverses, the accelerometer [153] is inadequate for reading the code using a probe that moves in the forward and backward direction. Regions of the code are read using eddy currents [230], which are the result of electrical current induced within the conductors of the coil, resulting in sensing changes in the magnetic field near the probe [110]. The probe also optionally includes one or more of the following components in any combination; velocity change compensators, temperature, pressure, radioactive, optical, magnetic, electric, and electromagnetic sensors. These sensors are provided for detecting, measuring, and distinguishing precise changes in position, material compositions, geological formations, speed, and acceleration within the fluid flowing in the casing.

In another embodiment, a single coil (as shown in FIG. 3A) resides in or on a probe which in this case is a sensor that moves at a known velocity to detect the width of the "ID bars" along the length of the casing. This probe is equipped with a "bar sensor", which is typically a cylindrical-shaped coil that is wrapped around the probe. The coil can be conductive, provide a magnetic field, or both, and can be made from a solid or metal (or other at least semi-conductive material) mesh screen. The materials selection of this portion of the probe is designed to be matched with certain sections of the casing. This design is necessary so that reading the code (provided by the changes of the material compositions in sections of the casing) is simple and occurs with limited or no interference.

Figure 3B:
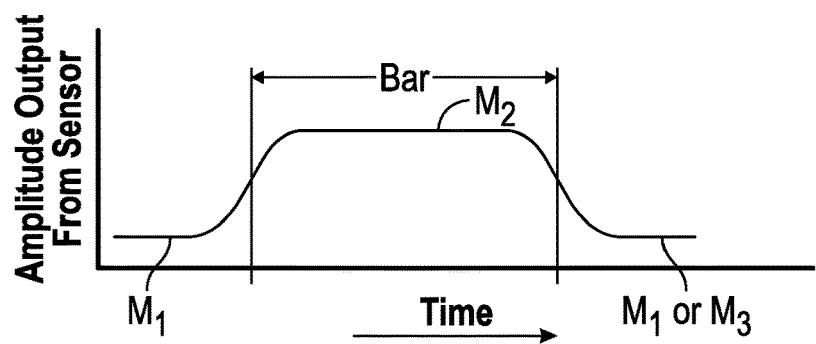
FIG. 3B is a sample of data output from the probe using a single sensor for sensing differences in a coded casing.

The plot in FIG. 3B indicates the amplitude of signals from the sensor as a function of time. The solid line shows the transition from Marker 2 (M2) that indicates a difference in material composition between Marker 1 (M1) and/or Marker 3 (M3). Each Marker will yield the same or different responses in comparison to other Markers. The slope of the solid line is proportional to the length of the Marker as it is read and sensed by the sensor. The slope shows the transition has some slope because of the width of the sensor. This is known as the aperture effect.

Clean detection of the code establishes precise resolute addresses along the casing at any point in time. Using the code received directly from the casing, separately or together with measuring the parameters described, allows for acting at specified addresses along the length of the casing with knowledge about this location before during or after any action is taken.

FIG. 4 is a visual example of how to determine the details of a coded region of the casing [105]. The coded region of the casing [105] is constructed of different material sections positioned along the casing [102] to provide "readable" variations in the casing [102] creating a code for an address. Variations in the coded region of the casing [105] are provided as short (S) and long (L) sections of compositional differences where a long (L) section of the coded region of the casing [105] is a length detected by the probe which is at least two (2) times that of the short (S) section of the coded region of the casing [105]. The length detected by the probe, L, of the short (S) section is generally about two (2) inches, thereby having a long (L) section of a length detected by the probe, 2L. Typically, the distance from the center of one sensor coil [125] to the center of the second (and subsequent) sensor coil(s) [125] is a distance of 1.5 times the length detected by the probe of the short (S) section of the coded region of the casing [105], or 1.5(L). The sensor coil(s) [125], when energized provide sensing capability to interpret the code from the coded region of the casing [105]. Engineering markings of the figure, for explanative and embodiment purposes, indicate preselected differences in the material composition of the casing (rings) in this section to be of the following order;

(i) non-conductive plastic,
(ii) synthetic resin
(iii) magnetic
(iv) synthetic resin
(v) non-conductive plastic (vi) synthetic resin
(vii) conductive material (metal)
(viii) synthetic resin
and finally a further type of non-conductive material.

Shorter and longer lengths of different material compositions correspond to patterns that collectively provide a code. These shorter and longer lengths are "read" by the probe inside the casing and correspond to the actual widths of the rings. Shorter or longer lengths "read" by the probe can be either conductive, non-conductive, magnetic, non-magnetic or insulative.

Conductive and/or magnetic sections are differentiated by the probe. Normally the longer lengths provide longer duration signals than the shorter lengths. By predetermining the lengths of sections of the rings inside the casing it is possible to tailor signal durations. For instance, if the long lengths are twice the dimension of the short lengths, the signal duration will be twice that of the short length.

Non-conductive and non-magnetic lengths (corresponding to widths of the rings) are indicated in FIG. 4 as white coded regions, W. Black coded regions, B, correspond to conductive and magnetic, conductive and non-magnetic, or magnetic and non-conductive material compositions. These are shown here to be Short White (SW) [402], Long Black (LB) [404], Short Black (SB) [406], and Long White (LW) [408]. Here, white regions correspond to readings of zero (0) and black regions correspond to readings of one (1). The short and long white coded regions differ in the duration of the absence of a reading. Conversely, the short black and long black coded regions differ in the duration of the presence of a reading.

This system and corresponding techniques provides accurate, reliable, continuous, reading of the code by the probe. As previously stated, the various material properties are a permanent feature of the casing, thereby requiring no maintenance.

III. Providing an Active Casing for a Coded Reader

In another embodiment, as a corollary to the probe, the casing can emit, receive, measure and/or distinguish a signal or a property residing in or sent from within the material composition(s) of the casing. The detectable properties and/or emanating signals from the sections of the casing are detected by using at least one reader, which, as described above, in one embodiment of the present invention, is a probe. In this aspect of the invention, the casing itself can provide an "active" ID code. The signals generated within the doped or circuitized material composition of the casing can be adjusted (via amplification or otherwise), as required, so that the probe can read specific intended lengths of the casing and provide exact addresses. By energizing the casing, an inactive reader which is coded in the same or similar manner as described for the coded casing above is also possible. In this case, the probe receives data so that pinpoint accuracy of specific probe addresses corresponding with the energized casing, is possible. Here, the casing provides two or more components that could be conductive and energized active markers. As indicated, here a probe must be provided that can accept data from imbedded sensors or circuits residing within the casing. The probe is coded and interprets the data from the casing. This allows for determining probe location and associated measurable parameters in that location. As before, the probe can be moving or stationary and can make measurements in a static or dynamic manner. The sensors/circuits within the casing may be imbedded in an outer or inner surface or most likely recessed below the surface, to increase the longevity of the use of any sensor/circuit in the downhole environment. The probe may also carry circuits or other devices that communicate effectively with those embedded in the casing.

FIG. 5 is an inverse embodiment of the code- and reader system [100] shown in FIGS. 1A-1E. Here, the system is depicted as being provided with a coded probe [500] and a casing [102] that contains sensor coil(s) [125] which are extended along the circumferential inner portion (surface) [502] of the casing [102] thereby turning the casing [102] into a "reader". The probe [110] is provided with a coded region (set of rings) of the probe [504]. The coded region of the probe [504] is provided with the same type of predetermined lengths and coding key as described for FIG. 4 above, specifically coding as before using Short White (SW) [402], Long Black (LB) [404], Short Black (SB) [406], and Long White (LW) [408]

IV. Providing an Active Coded Casing and One or More Active Coded Readers

In a fourth instance, a signal from one or more active coded probes (readers) can be used to actuate some portion of the doped or circuitized material composition residing within the casing. Actuation can also be provided by an active coded casing that has embedded energized circuits or materials which emit detectable signals (or both). In this embodiment, the coded probe can act as a transmitter/receiver, the coded casing can act as a transmitter/receiver or it is possible that both the coded probe and the coded casing are active and continuously communicating with each other. In this instance, this would provide additional data (from other codes or data sources) from specific locations along the casing and/or trigger additional actions. These actions can be directed toward or within the casing as well as toward or within the probe. In other words, the probe as well as the casing must be capable of distinguishing changes in strategically placed material properties in or on sections along the length of the casing or the probe. In addition, it is possible to actuate communication connections between a probe and another probe or between sections of the casing.

V. Ringed Sections with Different Material Compositions

Figure 6:
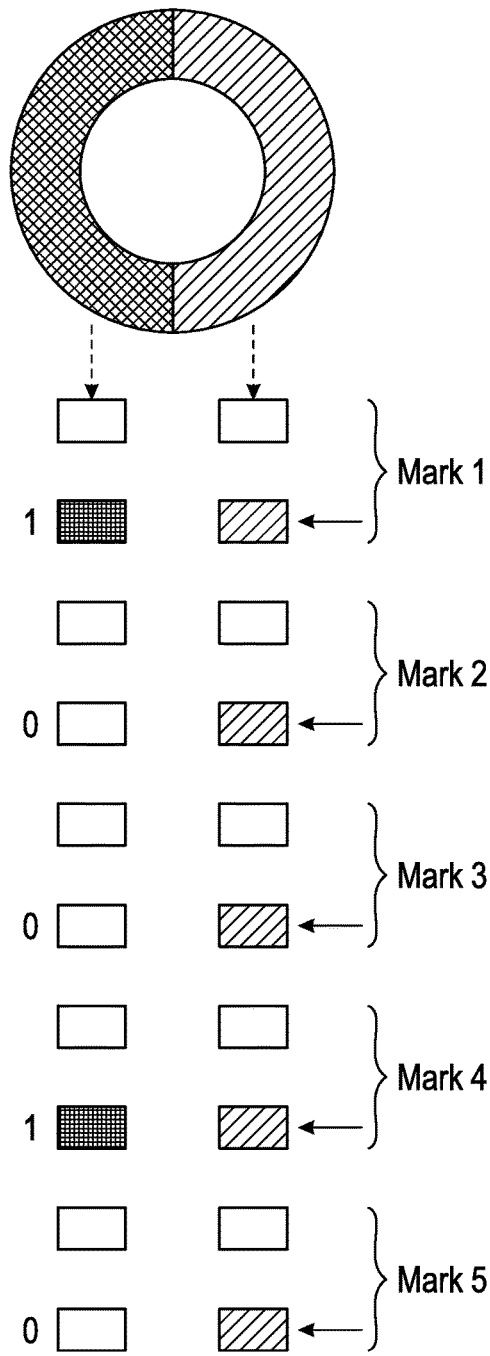
FIG. 6 is a schematic of multiple coded ringed sections and associated coded signals received by insertion of the ringed sections within a casing or a reader (probe).
Figure 7A:
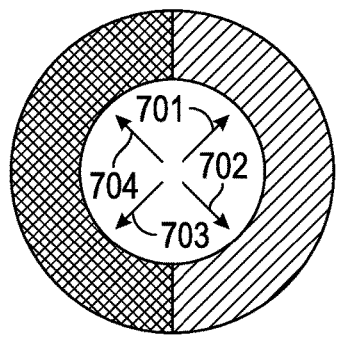
FIG. 7A depicts the use of multiple sensors for reading multiple coded rings.
Figure 7B:
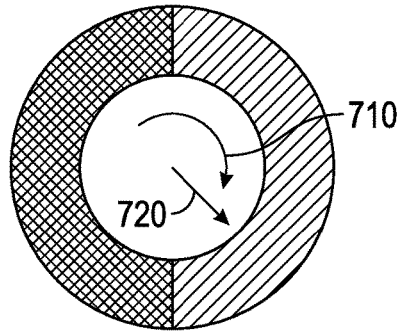
FIG. 7B depicts the output signals received when using a single moving sensor for reading multiple coded rings

As a corollary to (IV) above, it is also possible to provide ringed sections of the casing with rings having more than a single material composition. In this embodiment, the use of one or more (n) sensors allows for gathering more complete and precise data from these specially "doped" rings. FIGS. 6, 7A, and 7B graphically depict some of the possible arrangements of such rings and the consequential code sequencing that can occur using the split ring arrangements shown.

FIG. 6 depicts a "dual track sensor array". It illustrates a cross-section of a ring with the possibility of obtaining more than a single code sequence from a single ring by identifying material differences in the ring. Marks 1-5 are formed by using one method that allows for the code sequence to be digitized. In this case, the number of marks corresponds to the number of different detectable compositions making up the ring. Each mark is read from a different material section of the ring and represents a different "track". Each track is formed from sensing by a sensor (probe) that reads the track array. It is now possible to interpret a binary coded "0" and "1" system corresponding to sections of the ring being read by the probe in a continuous manner for synchronizing the data regarding material changes inside the ring as seen by the probe. For readers, this also allows for obtaining dual bar codes to distinguish certain features of the pipe, casing, etc. In FIG. 6, the Marks 1, 2, 3, 4 and 5 correspond to markers that provide readings (interpreted as a code) from a probe based on the position of the probe with respect to the material composition of the portion or region of the ring being read by the probe. For the sections depicted in FIG. 6, a probe reads regions within the rings that are conductive, non-conductive, magnetic, non-magnetic, etc. thus providing the different Marks that collectively comprise a code. To be able to read and interpret slight material compositional differences in each separate ring along a pipeline by doping certain sections of the ring is very useful.

FIG. 7A is a schematic drawing that represents the ability of one or more probes having at least N≥3 sensors reading the different (material) sections of the ring. The probe in this case is receiving (at least) data sets from the ring, rather than just single point data from a homogeneous ring. FIG. 7B depicts the use of a single sensor on a single probe which will rotate at some predetermined rate. Here the number of sensors (N) is N≥1 to ensure that the entire inner circumference of the ring is properly read. FIG. 7A is intended to illustrate (by the arrows designated as 701,702,703, and 704) sensors which can read multiple material sections of the ring, where N≥3 (as stated above). FIG. 7B is a schematic indicating a rotating sensor [710] that in this case is a single sensor [720] which, depending on the speed of rotation may be capable of providing as much or more information to be interpreted as code for the coded casing as that of the configuration shown in FIG. 7A.

One can envision that the system depicted in FIGS. 6 and 7A and 7B can become quite elaborate. To be able to read and interpret slight material compositional differences in each separate ring along a pipeline by doping certain sections of the ring is very useful. This can only be accomplished by and also providing a reader (probe) with enough sensors (or control of the sensors) to make multiple readings along the inner circumference of each of the "special" rings. The rings can be split in half, thirds, fourths, etc., and the readings will be based on the sensitivity of the probes used to read these differences. In any case, this method provides for being able to precisely know the exact address of the ringed section that the probe is sensing.

VI. General Use of the Systems, Methods, and Apparatuses

The operation of this system, method and associated apparatuses described, is dependent on the required usage. If for example, the determined ID code matches a target identification code, then one or more downhole structures can be actuated, managed, classified, identified, controlled, maintained, actuated, activated, deactivated, located, communicated with, reset, or installed. For example, a second downhole structure can be installed inside a first downhole structure or one can unlock the other, etc.

The present invention also relates to the apparatuses that can be used in the above described method as an overall system. For example, another aspect of the invention is a method of inventorying downhole equipment, and storing and retrieving identification codes for the inventoried equipment, as well as an inventory of services performed on the well. This method allows an operator to create a database of the identification codes of the pieces of equipment in the well and the location and/or orientation of each piece of equipment, and/or the equipment in which it is installed, and/or the services performed on the well. With such a database, an operator could determine (either before, during, or after well completion) the equipment profile of a well and plan out the downhole tasks.

One embodiment of this method comprises a reader unit that receives the signals transmitted by the identification transmitter units, decodes the signals to determine the identification codes corresponding thereto, and stores the identification codes in memory. This method can further comprise the step of creating a database for the well, the database comprising the stored identification codes. The method can also comprise reading from the database the identification codes for the well (e.g., the codes for equipment located in the well and/or the codes for services performed on the well). The identification codes read from the database can be used to perform at least one operation selected from the group consisting of managing, classifying, controlling, maintaining, actuating, activating, deactivating, locating, and communicating with at least one downhole structure in the well The system of the present invention has several benefits over prior art apparatus and methods. It provides a way of selectively installing, actuating, or inventorying downhole equipment at a desired time and/or at a desired location that is optionally independent of velocity of the probe (reader) or location of sensors. In addition, the coding is permanent in the manner described and is also essentially aperture insensitive in comparison with, for example RFID sensor systems. This system thereby provides lower cost, greater flexibility, better longevity and durability than other known existing techniques.

Another benefit of the present invention lies in the reduction of downhole tool manipulation time. In some cases, considerable downhole manipulation is performed to ensure that a tool is at the right point on the downhole jewelry or that the right action is performed. This time and effort can be eliminated or at least reduced by the present invention's ability to actuate or manipulate only when an exact (coded, i.e. bar coded) address has been reached or located so that an action can occur.

The present invention also makes use of non-acoustic transmission, such as radio frequency transmission, optical transmission, tactile transmission, magnetic transmission, and material conductivity differences for providing at least one identification code to locate, install, actuate, and/or manage downhole equipment in a subterranean wellbore.

Another embodiment of the invention makes use of a detachable, autonomous tool that can be released from the end of a supporting structure (e.g., coiled tubing, wireline, or completion hardware) while downhole or uphole, to then do some desired operation in another part of the well (e.g., spaced horizontally and/or or vertically from the point at which the tool separates from the supporting structure). The tool can later seek the end of the supporting structure, for example to enable it to be reattached, by homing in on the signal response from a transmitter unit embedded in the end of the supporting structure. Also, the tool can act as a repeater, actuator, or information relay device.

This relay of signal commands or information between autonomous agents optimized for submersible operations in different density fluids can use multiple autonomous agents and perform across multiple fluid interfaces. This relay of signal commands or information between autonomous agents can extend up or down-hole, between horizontal and vertical wellbores, and between multilateral wellbores and the main wellbore.

Another embodiment of the present invention uses the non-acoustic transmitter units to relay information from a downhole tool to a surface operator. In this embodiment, the downhole tool has monitors and records data such as temperature, pressure, time, or depth, for example. The tool can also record data describing the position or orientation of a piece of equipment, such as whether a sliding sleeve is open or closed. Further, the tool can record data such as whether downhole tools and equipment have been installed or actuated. The non-acoustic transmitter units can be dedicated to relaying a certain type of information or can be used to relay multiple data types. This enables the correlation of data such as the temperature and pressure at the time of detonation.

Once the desired information is acquired by the tool, a microprocessor on the tool determines what information should be sent to the surface. The pertinent information is then written to a read/write non-acoustic transmitter unit that is stored in the tool. The transmitter units can be stored in the tool in a variety of ways. For instance, the transmitter units can be installed into a spring-loaded column, much like the ammunition clip in a handgun.

Alternatively, the transmitter units can be stored around the perimeter of a revolving chamber. The manner in which the transmitter units are stored in the tool is not important, as long as the required numbers of tags are available for use and can be released to the surface.

After the pertinent information is written to a transmitter unit, the transmitter unit is released from the tool. It should be noted that the transmitter unit can be released either inside or outside of the tool depending upon the tool and the method of deployment. In one embodiment, when the transmitter unit is released, it is picked up by circulating fluid and carried to the surface. The transmitter unit is interrogated by a data acquisition device at the surface, at which time the information stored on the transmitter unit is downloaded. The microprocessor on the tool repeats the process with the additional transmitter units as directed by its programming.

In addition to tool-to-surface telemetry, as just described above, the non-acoustic transmitter units of the present invention can be used to send information from an operator at the surface to a tool located in the well. In this case, the transmitter unit is written to and released from the surface, circulated to the tool below, and returned to the surface. Once acquired by the tool, the information stored on the transmitter unit is downloaded for use by the microprocessor.

Depending on the programming of the tool microprocessor, a wide variety of instructions can be relayed from surface and carried out by the tool. Examples of possible instructions include how much to open a valve and whether or not to enter a multi-lateral, for example.

In another embodiment, the non-acoustic transmitter units of the present invention can be used autonomously without the necessity of a downhole tool. For example, the pumping fluid can be used to carry the transmitter units downhole and back to the surface through circulation. The individual transmitter units can receive and store data from transmitter units located downhole in tools, pipe casing, downhole equipment, etc. Once returned to the surface, the transmitter units can be analyzed to determine various operating conditions downhole. Such use provides continuous monitoring of wellbore conditions.

In another embodiment, the non-acoustic transmitter units of the present invention are used to autonomously actuate or install downhole tools and equipment. In this embodiment, non-acoustic transmitter units are dropped down the wellbore affixed to a drop ball, for example. As the non-acoustic transmitter units fall into proximity of non-acoustic receiver units located on the downhole tools and equipment, if the transmitted signal matches a predetermined identification code, the downhole tools and equipment are installed or actuated. It should be understood that both receiver units and transmitter units can be used to advantage being dropped down the wellbore. For example, a receiver unit affixed to a drop ball can carry information gathered from passing a transmitter unit affixed to the wellbore, tools, equipment, etc. and relay that information to a receiver unit located further downhole.

In yet another embodiment of the present invention, the non-acoustic transmitter units can be placed along the wellbore and correlated with formation or well parameters or completion characteristics at those locations. When the well is logged; a digital signature for the wellbore can be created to pinpoint depth in the wellbore.

In summary, the present invention provides apparatus and methods for managing, classifying, identifying, controlling, maintaining, actuating, activating, deactivating, locating, and communicating with downhole tools, jewelry, nipples, valves, gas-lift mandrels, packers, slips, sleeves and guns. The invention allows downhole tools to actuate only at the correct time and location and/or in the correct manner.

Although the present invention could be highly useful in any context, its benefits could be enhanced by a central organization that issues non-acoustic frequency identification units (encoding equipment serial numbers) to manufacturers of downhole components. This organization could also maintain a database of downhole tool identification codes/serial numbers of all components manufactured. Such a list of serial numbers could be classified or partitioned to allow for easy identification of the type and rating of any particular downhole component. Non-acoustic frequency transmitter units can store and transmit a signal corresponding to very large serial number strings that are capable of accommodating all necessary classes and ratings of equipment. Another suitable use of the invention includes packer landing verification.

The preceding description of specific embodiments of the present invention is not intended to be a complete list of every possible embodiment of the invention. Persons skilled in this field will recognize that modifications can be made to the specific embodiments described here that would be within the scope of the present invention.

We claim:

1. A method of installing, inventorying, actuating, and/or accessing down-hole equipment in a wellbore comprising;
   (i) marking a wellbore casing by inserting permanent components of selected material compositions within sections along a length of said casing within said wellbore, wherein said components and/or portions of an original section of said casing together function as unique readable active or passive markers,
   (ii) reading said markers, and;
   (iii) acting upon reading said markers using at least one reader and wherein said at least one reader is at least one probe and wherein said probe is an autonomous tool and wherein said at least one probe directs magnetic fields in a radial direction thereby measuring eddy currents and/or changes in eddy current intensity, and wherein said probe is shielded and optionally wherein said at least one probe is unshielded.

2. The method of claim 1, wherein inserting said markers in strategically placed locations along an axial and/or radial portion of said casing is creating one or more patterns or sequence of patterns and wherein said markers are comprised of components each possessing, independently, identical or different selected material compositions with cross sectional areas corresponding to each of said components.

3. The method of claim 2, wherein at least two or more of said components are rings made from different materials with distinct measurable property differences along said length of said casing, wherein said rings collectively function by providing a readable identification (ID) code created when said one or more patterns or sequence of patterns are read.

4. The method of claim 3, wherein said components are materials with properties selected from one or more or in any combination from a group consisting of electrically conductive, electrically resistive, electrically insulative, electrically capacitive, electrically inductive, magnetically permeable, magnetically non-permeable, magnetically polarized, sonically transmissive, sonically absorptive, optically reflective, optically absorptive, radiation absorptive, radiation emissive that exhibit one or more features of said materials and wherein said components can be rings comprising said materials.

5. The method of claim 3, wherein said readable ID code is read in precise locations along a length of said casing.

6. The method of claim 5, wherein said locations are a specific address corresponding to a feature either at the surface of, or embedded in, said casing.

7. The method of claim 1, wherein said markers appear as multiple readable bars to a reader that is reading said permanent components of said casing.

8. The method of claim 7, wherein said multiple readable bars comprise a spatial, binary, and/or bar code.

9. The method of claim 8, wherein reading by scanning said code with a reader provides an ability for finding a specific address along said casing and allows for carrying out an action at said address.

10. The method of claim 1, wherein said casing is a production collar within a borehole.

11. The method of claim 10, wherein said at least one probe is singularly, collectively, or in any combination, reading, transmitting, computing, recording, receiving, distinguishing, and/or measuring, at least a portion of one or more signals generated, emitted, and/or transmitted from said probe.

12. The method of claim 11, wherein said signals are being actively generated, emitted, and/or transmitted from said casing.

13. The method of claim 11, wherein said signals are passively generated, emitted, and/or transmitted from said casing.

14. The method of claim 13, wherein utilizing said probe and coded casing results in uninterrupted, unimpaired, detected material property change in said markers by using detectable changes in eddy current values received from said coded casing on a permanent basis.

15. The method of claim 10, wherein said collar is moving or stationary.

16. The method of claim 1, wherein said reader is one or more tethered probes.

17. The method of claim 1, wherein said at least one probe functions alone or in any combination as a plug, sensor, computer, recorder, detector, scanner, and/or barcode scanner.

18. The method of claim 17, wherein said at least one probe detects material property differences within said permanent components within said sections along said length of said casing.

19. The method of claim 1, wherein said probe is moving or stationary and wherein said signals are read while said probe is moving or stationary.

20. The method of claim 19, wherein said permanent components are placed as radial sections in and along said length of said casing.

21. The method of claim 1, wherein said at least one probe functions as a sensor that senses changes in said permanent components of selected material compositions along said length of said casing.

22. The method of claim 1, wherein said marking is accomplished while said casing is a production collar being installed in said wellbore.

23. The method of claim 3, wherein providing said readable ID code to a reader assists in identifying specific borehole features.

24. The method of claim 3, wherein providing said readable ID code to a reader assists in identifying specific features within a wellbore casing.

25. The method of claim 3, wherein providing said readable ID code assists in identifying branching of a borehole casing.

26. The method of claim 3, wherein said readable ID code is being read by said reader when said reader is moving in either a forward or backward direction.

27. A method of installing, inventorying, actuating, and/or accessing down-hole equipment in a wellbore comprising;
(i) marking a wellbore casing by inserting permanent components of selected material compositions within sections along a length of said casing within said wellbore, wherein said components and/or portions of an original section of said casing together function as unique readable active or passive markers,
(ii) reading said markers, and;
(iii) acting upon reading said markers using at least one reader and wherein said at least one reader is at least one probe and wherein said probe is an autonomous tool and wherein said at least one probe directs magnetic fields in a radial direction thereby measuring eddy currents and/or changes in eddy current intensity, and wherein said probe is shielded and optionally wherein said at least one probe is unshielded and wherein inserting said markers in strategically placed locations along an axial and/or radial portion of said casing is creating one or more patterns or sequence of patterns and wherein said markers are comprised of components each possessing, independently, identical or different selected material compositions with cross sectional areas corresponding to each of said components and wherein at least two or more of said components are rings made from different materials with distinct measurable property differences along said length of said casing, wherein said rings collectively function by providing a readable identification (ID) code created when said one or more patterns or sequence of patterns are read and wherein said readable ID code is read by a reader on a wireline so that said code is translated into data, wherein said data is sent to an uphole surface of a wellbore.

28. The method of claim 27, wherein said readable ID code is read by a reader on a wireline which is conveyed by jointed piping, or continuous tubing, to said uphole surface.

29. The method of claim 27, wherein said readable ID code is read by a reader on a wireline which is conveyed by a tractor or pipe crawler.

30. The method of claim 27, wherein said readable ID code is read by a reader connected to equipment not limited to measuring, computing, recording and/or actuating.

31. The method of claim 27, wherein said readable ID code is read by a reader moved by fluids in said wellbore and not limited to pumping and production of said fluids.

32. The method of claim 27, wherein said readable ID code is read by a reader moved by gravity.

33. The method of claim 27, wherein said readable ID code is read by a reader moved by buoyancy in said fluid.

34. The method of claim 27, wherein said readable ID code is read by a reader moved by self-propulsion.

35. The method of claim 27, wherein said reader takes action upon reading said readable ID code.

36. The method of claim 35, wherein said action releases mechanical keys.

37. The method of claim 35, wherein said action upon reading said readable ID code is actuating an electrical, electromagnetic, magnetic, pneumatic, hydraulic, radioactive, or fiber optic circuit.

38. The method of claim 35, wherein said action upon reading readable ID code initiates measurements.

39. The method of claim 35, wherein said action upon reading readable ID code is communicating with a unique identifier to equipment along a length of and including an uphole surface of said borehole.

40. The method of claim 39, wherein actuating communications is accomplished directly or remotely using wired or wireless communications.

\* \* \* \* \*